US012788572B2

(12) United States Patent
Fonte et al.

(10) Patent No.: US 12,788,572 B2
(45) **Date of Patent: *Nov. 10, 2026**

(54) ARTHROPLASTY IMPLANT SYSTEMS FOR GENERATING AND APPLYING DYNAMIC COMPRESSION

(71) Applicant: ARTHREX, INC., Naples, FL (US)

(72) Inventors: Matthew Fonte, Concord, MA (US); Adam Garlock, Naples, FL (US)

(73) Assignee: ARTHREX, INC., Naples, FL (US)

( * ) Notice: Subject to any disclaimer, the term of this patent is extended or adjusted under 35 U.S.C. 154(b) by 1114 days.

This patent is subject to a terminal disclaimer.

(21) Appl. No.: 17/488,788

(22) Filed: Sep. 29, 2021

(65) Prior Publication Data

US 2022/0015917 A1 Jan. 20, 2022

Related U.S. Application Data

(63) Continuation of application No. 16/551,938, filed on Aug. 27, 2019, now Pat. No. 11,141,283, which is a continuation of application No. 16/030,154, filed on Jul. 9, 2018, now Pat. No. 10,912,652.

(51) Int. Cl.
*A61F 2/42* (2006.01)
*A61F 2/30* (2006.01)

(52) U.S. Cl.
CPC ........ *A61F 2/4202* (2013.01); *A61F 2/30749* (2013.01); *A61F 2002/30074* (2013.01); *A61F 2002/30092* (2013.01); *A61F 2002/30433* (2013.01); *A61F 2002/3055* (2013.01);
(Continued)

(58) Field of Classification Search
CPC ................ A61F 2/30749; A61F 2/4202; A61F 2002/4207; A61F 2002/4205; A61F 2002/30563; A61F 2/42; A61F 2002/30092; A61F 2002/30433; A61F 2002/3055; A61B 17/7291; A61B 17/72; A61B 2017/00867
See application file for complete search history.

(56) References Cited

U.S. PATENT DOCUMENTS 3,441,017 A 4/1969 Kaessmann
3,986,504 A 10/1976 Avila
(Continued)

FOREIGN PATENT DOCUMENTS

EP 1550418 A1 7/2005
FR 2289155 A1 5/1976
(Continued)

OTHER PUBLICATIONS

Notice of Reasons for Rejection for JP Application No. 2021-500865 dated Jun. 12, 2023.
(Continued)

*Primary Examiner* — Thomas C Barrett
*Assistant Examiner* — Teresa M Dudden
(74) *Attorney, Agent, or Firm* — Carlson, Gaskey & Olds, P.C.

(57) ABSTRACT

Arthroplasty implant systems and procedures are disclosed herein. In an embodiment, an arthroplasty implant of an arthroplasty system includes a shape memory material connecting member attached to two points of fixation of the arthroplasty implant.

20 Claims, 5 Drawing Sheets

(52) U.S. Cl.
CPC ............... *A61F 2002/30563* (2013.01); *A61F 2002/4205* (2013.01); *A61F 2002/4207* (2013.01)

(56) References Cited

U.S. PATENT DOCUMENTS

| | | | | |
|---|---|---|---|---|
| 4,166,292 | A * | 9/1979 | Bokros | A61F 2/32 623/21.18 |
| 4,875,475 | A | 10/1989 | Comte et al. | |
| 5,034,012 | A | 7/1991 | Frigg | |
| 5,263,955 | A | 11/1993 | Baumgart et al. | |
| 5,352,228 | A | 10/1994 | Kummer et al. | |
| 5,505,734 | A | 4/1996 | Caniggia et al. | |
| 5,536,270 | A | 7/1996 | Songer | |
| 6,648,890 | B2 | 11/2003 | Culbert et al. | |
| 6,786,908 | B2 | 9/2004 | Hover et al. | |
| 6,932,819 | B2 | 8/2005 | Wahl et al. | |
| 7,410,488 | B2 | 8/2008 | Janna et al. | |
| 7,534,246 | B2 * | 5/2009 | Reiley | A61B 17/15 623/21.18 |
| 7,942,876 | B2 | 5/2011 | Hack | |
| 7,985,222 | B2 | 7/2011 | Gall et al. | |
| 8,118,952 | B2 | 2/2012 | Gall et al. | |
| 8,162,942 | B2 | 4/2012 | Coati et al. | |
| 8,439,916 | B2 | 5/2013 | Coati et al. | |
| 8,460,293 | B2 | 6/2013 | Coati et al. | |
| 8,491,583 | B2 * | 7/2013 | Gall | A61B 17/7241 606/62 |
| RE44,501 | E | 9/2013 | Janna et al. | |
| 8,876,821 | B2 | 11/2014 | Kinmon | |
| 8,915,917 | B2 | 12/2014 | Doherty et al. | |
| 9,138,266 | B2 | 9/2015 | Stauch | |
| 9,308,031 | B2 | 4/2016 | Elghazaly et al. | |
| 9,320,551 | B2 | 4/2016 | Frank et al. | |
| RE46,008 | E | 5/2016 | Janna et al. | |
| 9,351,771 | B2 | 5/2016 | Gorsline et al. | |
| RE46,078 | E | 7/2016 | Janna et al. | |
| 9,381,052 | B2 | 7/2016 | Ziran | |
| 9,440,009 | B2 | 9/2016 | Armbruster et al. | |
| 9,445,850 | B2 | 9/2016 | Kinmon | |
| 9,480,506 | B2 | 11/2016 | Zehtab et al. | |
| 9,737,347 | B2 | 8/2017 | Schlienger et al. | |
| 9,770,274 | B2 | 9/2017 | Pool et al. | |
| 9,861,413 | B2 | 1/2018 | Palmer et al. | |
| 9,931,146 | B2 | 4/2018 | Gorsline et al. | |
| 9,987,144 | B2 * | 6/2018 | Seifert | A61F 2/447 |
| 10,912,652 | B2 * | 2/2021 | Fonte | A61B 17/7291 |
| 11,109,903 | B2 | 9/2021 | Leibowitz | |
| 11,141,283 | B2 * | 10/2021 | Fonte | A61B 17/72 |
| 11,801,076 | B2 | 10/2023 | Vicenzi et al. | |
| 12,004,787 | B2 | 6/2024 | Garlock | |
| 2002/0055744 | A1 | 5/2002 | Reiley | |
| 2005/0216007 | A1 | 9/2005 | Woll et al. | |
| 2006/0229730 | A1 * | 10/2006 | Railey | A61B 17/15 623/23.44 |
| 2006/0293683 | A1 | 12/2006 | Stauch | |
| 2007/0123878 | A1 * | 5/2007 | Shaver | A61B 17/72 606/64 |
| 2007/0213725 | A1 | 9/2007 | Hack | |
| 2007/0233100 | A1 * | 10/2007 | Metzinger | A61B 17/748 606/62 |
| 2008/0221577 | A1 | 9/2008 | Elghazaly | |
| 2010/0010490 | A1 | 1/2010 | Brigido | |
| 2010/0268285 | A1 | 10/2010 | Tipirneni et al. | |
| 2011/0004212 | A1 * | 1/2011 | Gall | A61B 17/7225 606/62 |
| 2011/0054473 | A1 | 3/2011 | Brigido | |
| 2011/0160728 | A1 | 6/2011 | Blitz | |
| 2011/0230883 | A1 | 9/2011 | Zahrly et al. | |
| 2011/0301653 | A1 * | 12/2011 | Reed | A61F 2/4225 606/319 |
| 2012/0130370 | A1 | 5/2012 | Kinmon | |
| 2012/0136356 | A1 | 5/2012 | Doherty et al. | |
| 2012/0209265 | A1 | 8/2012 | Pool | |
| 2012/0209268 | A1 | 8/2012 | Overes | |
| 2012/0239038 | A1 | 9/2012 | Saravia et al. | |
| 2013/0012942 | A1 | 1/2013 | Nelson et al. | |
| 2013/0085502 | A1 | 4/2013 | Harrold | |
| 2013/0116693 | A1 | 5/2013 | Nelson et al. | |
| 2013/0325010 | A1 | 12/2013 | Prien et al. | |
| 2014/0005669 | A1 | 1/2014 | Graham | |
| 2014/0114311 | A1 | 4/2014 | Pool et al. | |
| 2014/0142575 | A1 | 5/2014 | Biedermann et al. | |
| 2014/0228845 | A1 | 8/2014 | Gorsline et al. | |
| 2015/0230843 | A1 | 8/2015 | Palmer | |
| 2016/0058483 | A1 | 3/2016 | Stauch | |
| 2016/0199109 | A1 * | 7/2016 | Zehtab | A61B 17/7233 606/64 |
| 2017/0049575 | A1 * | 2/2017 | Dhillon | A61F 2/4202 |
| 2017/0100163 | A1 | 4/2017 | Palmer et al. | |
| 2017/0128221 | A1 | 5/2017 | Wong | |
| 2017/0172624 | A1 | 6/2017 | Brunner et al. | |
| 2017/0296241 | A1 | 10/2017 | Garlock et al. | |
| 2018/0092677 | A1 | 4/2018 | Peterson et al. | |
| 2021/0038269 | A1 | 2/2021 | Kearns | |
| 2023/0240729 | A1 | 8/2023 | Eceviz et al. | |

FOREIGN PATENT DOCUMENTS

| | | | |
|---|---|---|---|
| JP | S61276553 | A | 12/1986 |
| WO | 2009/108194 | A1 | 9/2009 |
| WO | 2011/008739 | A2 | 1/2011 |
| WO | 2017181174 | A1 | 10/2017 |

OTHER PUBLICATIONS

International Preliminary Report on Patentability for PCT Application No. PCT/US2017/027910, mailed Oct. 25, 2018.

International Search Report and Written Opinion of the International Searching Authority for International Application No. PCT/US2017/027910 dated Sep. 6, 2017.

International Search Report and Written Opinion of the International Searching Authority for International application No. PCT/US2019/040783 dated Sep. 24, 2019.

International Preliminary Report on Patentability for International application No. PCT/US2019/040783 dated Jan. 21, 2021.

* cited by examiner

ARTHROPLASTY IMPLANT SYSTEMS FOR GENERATING AND APPLYING DYNAMIC COMPRESSION

CROSS-REFERENCE TO RELATED APPLICATION

This is a continuation of U.S. patent application Ser. No. 16/551,938, filed on Aug. 27, 2019, which is a continuation of U.S. patent application Ser. No. 16/030,154, filed on Jul. 9, 2018, now U.S. Pat. No. 10,912,652, the disclosures of which are incorporated herein by reference in their entirety.

BACKGROUND

This disclosure relates to arthroplasty implant systems, and more particularly to arthroplasty implants that are capable of applying dynamic compression between the arthroplasty implants and surrounding bones.

During a partial or total joint arthroplasty procedure, parts of a joint, such as an ankle, hip, shoulder, or knee joint, for example, may be replaced with one or more arthroplasty implants (e.g., artificial components or prostheses). Arthroplasty implants may loosen over time, which can result in undesirable implant migration.

SUMMARY

This disclosure relates to arthroplasty implant systems for performing arthroplasty procedures. Arthroplasty implant systems and procedures are designed to restore function of a deteriorated joint. The arthroplasty implant systems described herein can provide dynamic compression between an arthroplasty implant and a bone.

An arthroplasty implant system includes, inter alia, an arthroplasty implant including a stem extending along a longitudinal axis between a proximal portion and a distal portion. A proximal slider may be housed inside the proximal portion of the stem, and a distal slider may be housed inside the distal portion of the stem. A rod may connect to both the proximal slider and the distal slider. The rod can be a shape memory material such as Nitinol. A first opening may be located within the proximal portion of the stem, and a first screw may be received through the first opening and the proximal slider. A second opening may be located within the distal portion of the stem, and a second screw may be received through the second opening and the distal slider. At least one of the first opening and the second opening may be an elongated slot. A set screw may be removably inserted into either the proximal slider or the distal slider. The set screw may be removed from the proximal slider or the distal slider to allow the rod to superelastically shorten.

An arthroplasty implant system can also include, inter alia, an a proximal interlocking fixation body located at least partially inside the proximal portion and a distal interlocking fixation body located at least partially inside the distal portion. A shape memory material connecting member may be attached to the proximal interlocking fixation body and the distal interlocking fixation body.

A method for performing an arthroplasty procedure includes, inter alia, inserting an arthroplasty implant within a bone of a joint, inserting a first fixation device through a first opening of the arthroplasty implant, inserting a second fixation device through a second opening of the arthroplasty implant, and removing a holding device, such as a set screw, from the arthroplasty implant. The arthroplasty implant may include a shape memory material connecting member that is pre-stretched from an unstretched position to a stretched position prior to inserting the arthroplasty implant. Removing the holding device may superelastically shorten the shape memory material connecting member from the stretched position toward the unstretched position, thereby moving the arthroplasty implant and the bone into compressive engagement with one another.

DETAILED DESCRIPTION

Figure 1:
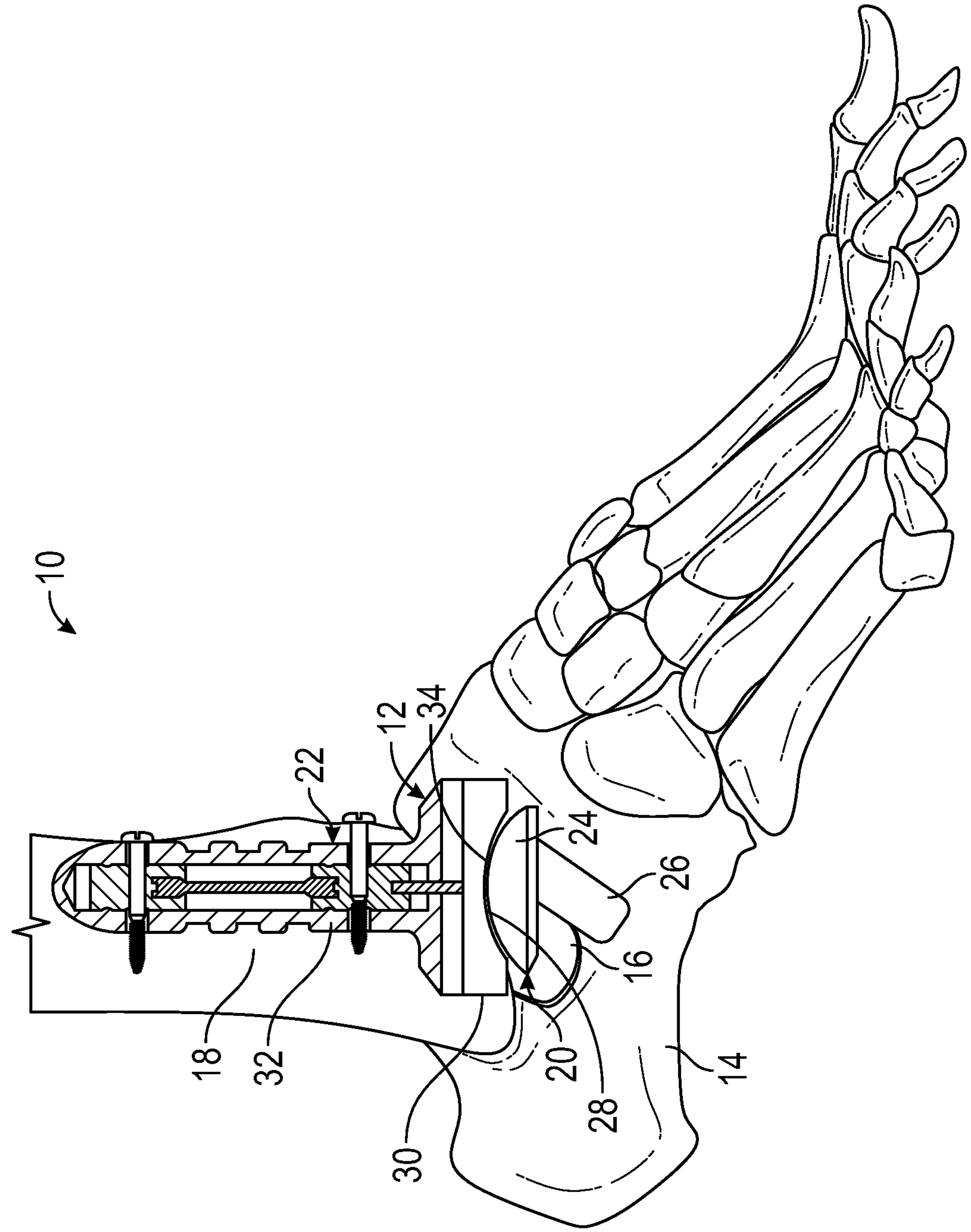
FIG. 1 illustrates a joint of the human musculoskeletal system.
Figure 2:
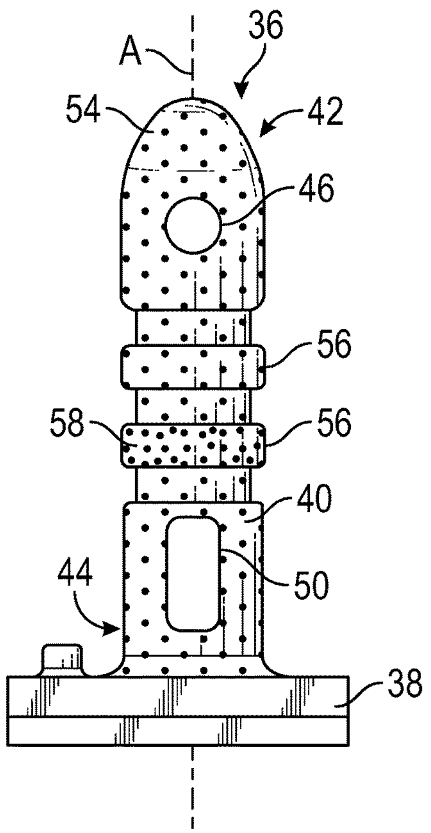
FIG. 2 is a front view of an arthroplasty implant. The arthroplasty implant is part of an arthroplasty implant system designed for performing arthroplasty procedures.

This disclosure describes arthroplasty implant systems that include arthroplasty implants, such as stemmed implants, for performing arthroplasty procedures within joints. Arthroplasty implants of this disclosure are capable of generating and maintaining a compressive load for a prolonged period of time while healing of the joint occurs. A dynamically created compressive force actively loads the arthroplasty implant and a surrounding bone into further engagement with one another, thereby applying constant compression between the arthroplasty implant and the bone. The arthroplasty implants described herein are therefore less prone to migration over time as compared to known arthroplasty implants.

An arthroplasty implant system includes, inter alia, an arthroplasty implant including a stem extending along a longitudinal axis between a proximal portion and a distal portion. A proximal slider may be housed inside the proximal portion of the stem, and a distal slider may be housed inside the distal portion of the stem. A rod may connect to both the proximal slider and the distal slider. The rod can be a shape memory material such as Nitinol. A first opening may be located within the proximal portion of the stem, and a first screw may be received through the first opening and the proximal slider. A second opening may be located within the distal portion of the stem, and a second screw may be received through the second opening and the distal slider. At least one of the first opening and the second opening may be an elongated slot. A set screw may be removably inserted into either the proximal slider or the distal slider. The set screw may be removed from the proximal slider or the distal slider to allow the rod to superelastically shorten.

A proximal interlocking fixation body may be located at least partially inside the proximal portion, and a distal interlocking fixation body may be located at least partially inside the distal portion. A shape memory material connecting member may be attached to the proximal interlocking fixation body and the distal interlocking fixation body.

In a further embodiment, a stem of an arthroplasty implant may include at least one opening configured to receive a fixation device.

In a further embodiment, a proximal portion of a stem of an arthroplasty implant includes a first opening and a distal portion of the stem includes a second opening. One of the first opening and the second opening may be an elongated slot and the other of the first opening and the second opening may be a round opening.

In a further embodiment, a stem of an arthroplasty implant extends from a base, and at least one of the stem and the base may be coated with a porous material.

In a further embodiment, a first opening may be located within a proximal portion of a stem of an arthroplasty implant and receives a first screw, and a second opening may be located within a distal portion of the stem and receives a second screw.

In a further embodiment, a shape memory material connecting member of an arthroplasty implant may be a rod made of Nitinol (NiTi).

In a further embodiment, a shape memory material connecting member of an arthroplasty implant may include an elongated shaft extending between a first threaded portion and a second threaded portion.

In a further embodiment, at least one of a proximal interlocking fixation body and a distal interlocking fixation body may translate within a cannulation of a stem of an arthroplasty implant.

In a further embodiment, a set screw may be removably connected to either a proximal interlocking fixation body or a distal interlocking fixation body of an arthroplasty implant.

In a further embodiment, a set screw may be removed from a proximal interlocking fixation body or a distal interlocking fixation body to allow a shape memory material connecting member of an arthroplasty implant to superelastically shorten from a stretched position toward an unstretched position.

A method for performing an arthroplasty procedure includes, inter alia, inserting an arthroplasty implant within a bone of a joint, inserting a first fixation device through a first opening of the arthroplasty implant, inserting a second fixation device through a second opening of the arthroplasty implant, and removing a holding device, such as a set screw, from the arthroplasty implant. The arthroplasty implant may include a shape memory material connecting member that is pre-stretched from an unstretched position to a stretched position prior to inserting the arthroplasty implant. Removing the holding device may superelastically shorten the shape memory material connecting member from the stretched position toward the unstretched position, thereby moving the arthroplasty implant and the bone into compressive engagement with one another.

In a further embodiment, an arthroplasty implant may be inserted into an ankle joint, a shoulder joint, a hip joint, or a knee joint.

In a further embodiment, prior to inserting an arthroplasty implant, a passage may be reamed into a bone, such as a tibia or other long bone, for accommodating portions of the arthroplasty implant, such as a stemmed portion.

In a further embodiment, a first fixation device of an arthroplasty implant is a first screw, bolt, or peg and a second fixation device of the arthroplasty implant is a second screw, bolt, or peg.

In a further embodiment, a shape memory material connecting member of an arthroplasty implant may connect between a proximal interlocking fixation body and a distal interlocking fixation body of the arthroplasty implant, and a set screw may be connected to either the proximal interlocking fixation body or the distal interlocking fixation body. The set screw may be unscrewed from the proximal interlocking fixation body or the distal interlocking fixation body, thereby permitting the proximal interlocking fixation body or the distal interlocking fixation body to translate inside the arthroplasty implant.

In a further embodiment, permitting a proximal interlocking fixation body or a distal interlocking fixation body to translate inside an arthroplasty implant may result in moving a shape memory material connecting member from a stretched position back toward an unstretched position.

In a further embodiment, either a proximal interlocking fixation body or a distal interlocking fixation body of an arthroplasty implant may be fixed from movement prior to removing a set screw from the arthroplasty implant.

In a further embodiment, inserting a first fixation device through a first opening of an arthroplasty implant may include passing the first fixation device through a non-threaded opening of a proximal interlocking fixation body housed inside a stem of the arthroplasty implant.

In a further embodiment, inserting a second fixation device through a second opening of an arthroplasty implant may includes passing the second fixation device through a non-threaded opening of a distal interlocking fixation body housed inside a stem of the arthroplasty implant.

FIG. 1 schematically illustrates a joint 10 of the human musculoskeletal system that has been repaired or replaced by an arthroplasty implant system 12. In an embodiment, the arthroplasty implant system 12 is configured for implantation into an ankle joint. However, the arthroplasty implant systems 12 of this disclosure could be used to repair or replace other joints within the scope of this disclosure (e.g., knee joint, hip joint, shoulder joint, wrist joint, etc.). In an embodiment, the teachings of this disclosure are applicable to any arthroplasty implant system that utilizes one or more stemmed implants that are implanted inside elongated bones.

The joint 10 of FIG. 1 includes, among other bones, a calcaneus 14, a talus 16, and a tibia 18. Over time, one or more of these bones of the joint 10 may become arthritic, diseased, or otherwise deteriorated to the point that a partial or total arthroplasty procedure may become necessary in order to restore the function of the joint 10. During such arthroplasty procedures, one or more parts of the joint 10 may be replaced with one or more arthroplasty implants (e.g., artificial components or prostheses).

In an embodiment, the arthroplasty implant system 12 includes a talar component 20 configured for installation into portions of the talus 16 and/or the calcaneus 14, and a tibial component 22 configured for installation into the tibia 18. The talar component 20 may include a dome 24 and a stem 26 (i.e., arthroplasty implants). The dome 24 may establish a first articulating surface 28 of the arthroplasty implant system 12. The stem 26 may extend from the dome 24 into the talus 16 and the calcaneus 14 to anchor the talar component 20 within the joint 10.

The tibial component 22 may include a tray 30 and a stemmed implant 32 (i.e., arthroplasty implants). The tray 30 may establish a second articulating surface 34 of the arthroplasty implant system 12. The stemmed implant 32 may connect to the tray 30 and may extend into the tibia 18 to anchor the tibial component 22 within the joint 10. In an embodiment, the first articulating surface 28 of the talar component 20 and the second articulating surface 34 of the tibial component 22 are sized and shaped to articulate relative to one another. The articulating surfaces 28, 34 may therefore replace the native articulating surfaces of the joint 10, which have been removed during the arthroplasty procedure, to restore the native kinematic motion and functionality of the joint 10.

Although ankle joint arthroplasty is generally described above and throughout this disclosure as one exemplary arthroplasty procedure, this disclosure is not intended to be limited to ankle arthroplasty procedures. An implant as disclosed herein can also be used in shoulder, hip, and knee arthroplasty procedures, for example.

FIGS. 2, 3, 4, and 5 illustrate an exemplary arthroplasty implant 36 of an arthroplasty implant system, such as the arthroplasty implant system 12 of FIG. 1, for example. In an embodiment, the arthroplasty implant 36 is a stemmed implant of an arthroplasty implant system.

The exemplary arthroplasty implant 36 may include a base 38 and a stem 40 that protrudes outwardly from the base 38. The stem 40 may extend along a longitudinal axis A between a proximal portion 42 and a distal portion 44. In an embodiment, the arthroplasty implant 36 is configured such that, once implanted within the joint 10 of FIG. 1, the proximal portion 42 of the stem 40 extends into the tibia 18 of the joint 10 and is located further away from the talus 16 than the distal portion 44.

The stem 40 may be configured as a sleeve for housing other components of the arthroplasty implant 36 (discussed further below). In an embodiment, the arthroplasty implant 36 is made of a titanium alloy, such as Ti-6Al-4V. However, other materials are also contemplated within the scope of this disclosure.

The stem 40 may include multiple openings for receiving fixation devices, such as screws, bolts, pegs, etc., for fixating the arthroplasty implant 36 within a joint. For example, the proximal portion 42 of the stem 40 may include a first opening 46 that is configured to receive a first fixation device 48 (e.g., a first screw, bolt, or peg) for fixating the arthroplasty implant 36 to the tibia 18. In an embodiment, the first opening 46 is a round opening that extends completely through the stem 40 at a perpendicular angle relative to the longitudinal axis A.

The distal portion 44 of the stem 40 may include a second opening 50 that is configured to receive a second fixation device 52 (i.e., a second screw, bolt, or peg) for fixating the arthroplasty implant 36 to the tibia 18. In an embodiment, the second opening 50 is an elongated slot that extends completely through the stem 40 at a perpendicular angle relative to the longitudinal axis A. The second opening 50 may extend in parallel with the first opening 46.

The stem 40 of the arthroplasty implant 36 may additionally include a domed tip 54 that establishes a proximal most tip of the proximal portion 42. The domed tip 54 simplifies implantation of the stem 40 within a bone passage. A plurality of ribs 56 may optionally protrude from an external surface of the stem 40 for increasing the fixation strength of the stem 40.

One or more portions of the arthroplasty implant 36 may be coated with a porous material 58 (see FIGS. 2-3) that promotes bone ingrowth and osseointegration with the surrounding bone subsequent to implantation. In an embodiment, the porous material 58 is a biofoam material. The porous material 58 may be made of any porous biomaterial, including but not limited to, porous titanium and porous tantalum. The porous material 58 may be applied to the base 38, the stem 40, or both.

Figure 4:
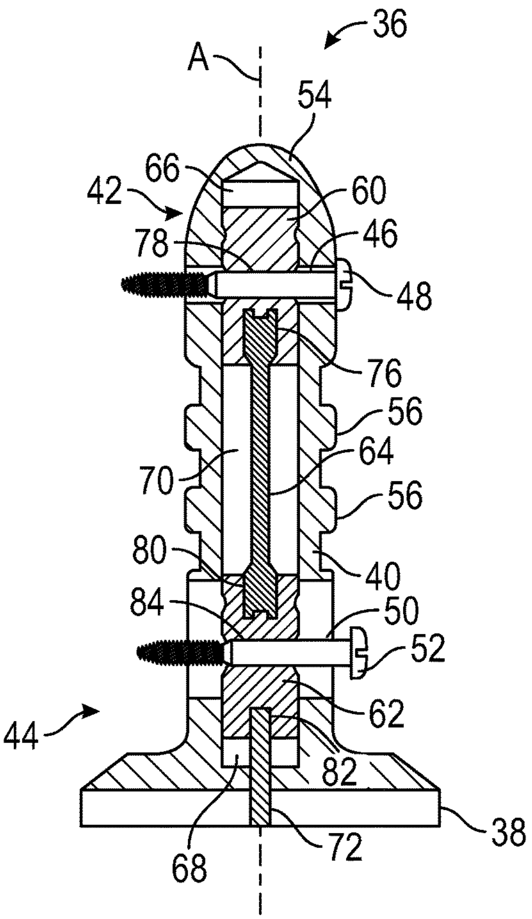
FIG. 4 is a cross-sectional view taken through section A-A of FIG. 3.
Figure 3:
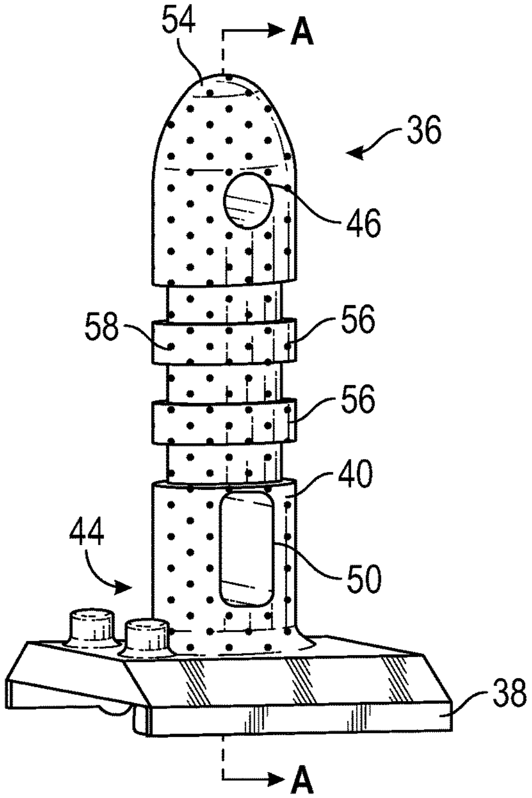
FIG. 3 is a perspective view of the arthroplasty implant of FIG. 2.
Figure 5:
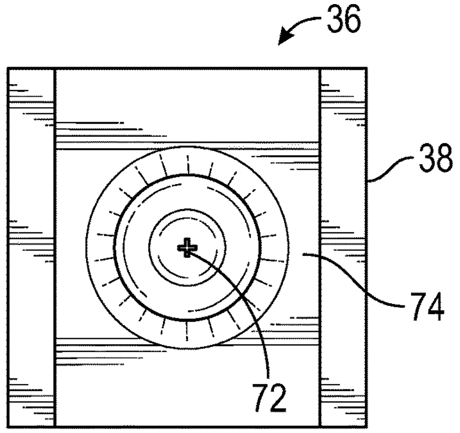
FIG. 5 is a bottom view of the arthroplasty implant of FIG. 2.

As best illustrated by the cross-sectional view of FIG. 4, the stem 40 of the arthroplasty implant 36 may house a proximal interlocking fixation body 60, a distal interlocking fixation body 62, and a shape memory material connecting member 64. The proximal interlocking fixation body 60 may be slidably received within a first cannulation 66 formed in the stem 40 and is at least partially exposed within the first opening 46, the distal interlocking fixation body 62 may be slidably received within a second cannulation 68 formed in the stem 40 and is at least partially exposed within the second opening 50, and the shape memory material connecting member 64 may be received within a third cannulation 70 formed in the stem 40 and is connected (e.g., threadably engaged) to both the proximal interlocking fixation body 60 and the distal interlocking fixation body 62. In an embodiment, the proximal interlocking fixation body 60 and the distal interlocking fixation body 62 are configured as sliders that may move inside the stem 40.

In an embodiment, the proximal interlocking fixation body 60 and the distal interlocking fixation body 62 are made of a titanium alloy, such as Ti-6Al-4V. In another embodiment, the proximal interlocking fixation body 60 and the distal interlocking fixation body 62 are proximal and distal sliders, respectively, of the arthroplasty implant 36.

In another embodiment, the shape memory material connecting member 64 may be configured as a rod, e.g., a rod made of Nitinol (NiTi). However, the shape memory material connecting member 64 could have other shapes and configurations, and other superelastic materials (e.g., materials capable of exhibiting superelasticity and/or a temperature-induced shape changes) can be used to construct the shape memory material connecting member 64.

The arthroplasty implant 36 may additionally include a holding device 72, which may be used as a device for enacting the superelastic qualities of the shape memory material connecting member 64. In an embodiment, the holding device 72 is a set screw that is removably attached to the distal interlocking fixation body 62 and extends to a location outside of the stem 40 where it can be accessed on a bottom surface 74 of the base 38 (see, e.g., FIG. 5). However, other types of holding devices could alternatively be used within the scope of this disclosure.

The shape memory material connecting member 64 may be pre-stretched to stretched position and then held in the stretched position by the holding device 72. After implantation of the arthroplasty implant 36 within a bone tunnel, the holding device 72 may be unscrewed or otherwise released from the distal interlocking fixation body 62. Releasing the holding device 72 allows the distal interlocking fixation body 62 to slide within the second cannulation 68, thereby allowing the shape memory material connecting member 64 to superelastically shorten toward an unstretched position. Releasing the holding device 72 therefore causes the shape memory material connecting member 64 to want to return toward the unstretched position. The arthroplasty implant 36 is therefore equipped to force itself into improved engagement with the bone by applying a constant dynamic compression force between the arthroplasty implant 36 and the surrounding bone.

Figure 6A:
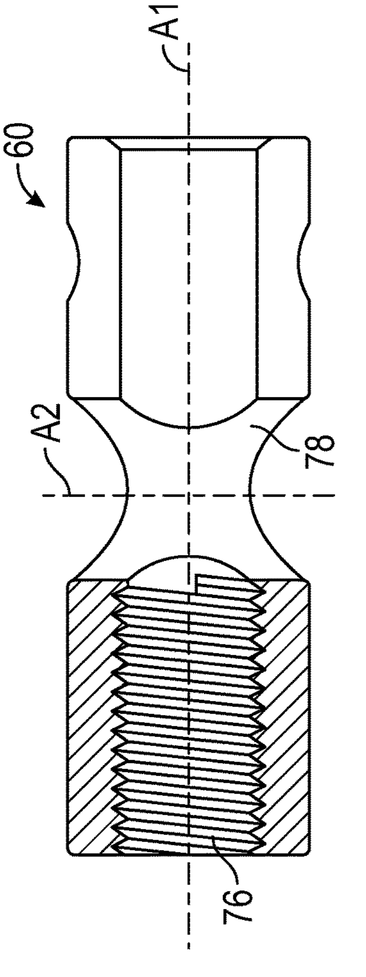
FIG. 6A illustrates a proximal interlocking fixation body of the arthroplasty implant of FIG. 2.
Figure 6B:
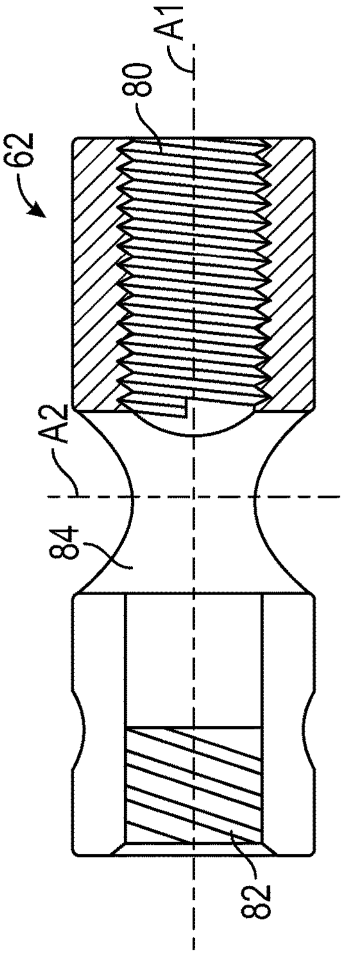
FIG. 6B illustrates a distal interlocking fixation body of the arthroplasty implant of FIG. 2.

FIGS. 6A and 6B illustrate additional features of the proximal interlocking fixation body 60 and the distal interlocking fixation body 62, respectively. Referring first to FIG.

6A, the proximal interlocking fixation body 60 may include a threaded opening 76 extending along a first axis A1 and a non-threaded opening 78 extending along a second axis A2. In an embodiment, the second axis A2 is perpendicular to the first axis A1. The threaded opening 76 may receive a portion of the shape memory material connecting member 64 (see FIG. 4), and the non-threaded opening 78 may receive the first fixation device 48 (see FIG. 4). In an implanted position of the arthroplasty implant 36, the threaded opening 76 is positioned distally of the non-threaded opening 78.

Referring now to FIG. 6B, the distal interlocking fixation body 62 may include a first threaded opening 80 and a second threaded opening 82 extending along a first axis A1, and a non-threaded opening 84 extending along a second axis A2. In an embodiment, the second axis A2 is perpendicular to the first axis A1. The first threaded opening 80 may receive a portion of the shape memory material connecting member 64 (see FIG. 4), the second threaded opening 82 may receive the holding device 72, and the non-threaded opening 84 may receive the second fixation device 52 that extends through the second opening 50 of the stem 40 (see FIG. 4). In an implanted position of the arthroplasty implant 36, the first threaded opening 80 is positioned proximally of the non-threaded opening 84, and the second threaded opening 82 is positioned distally of the non-threaded opening 84.

Figure 7:
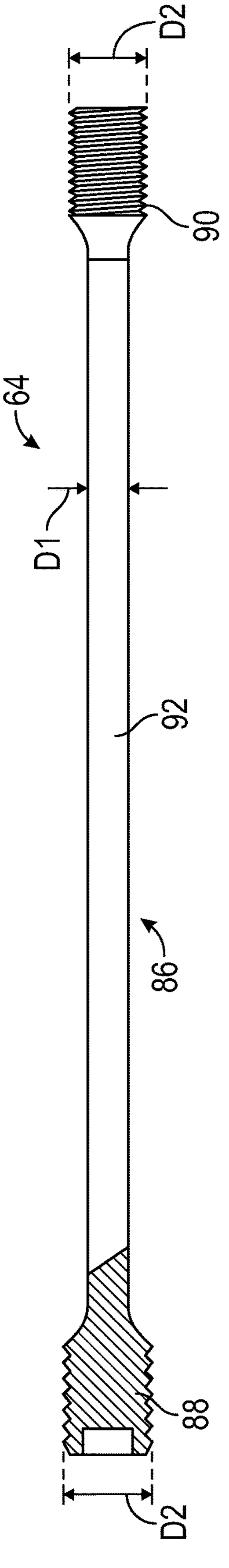
FIG. 7 illustrates a shape memory material connecting member of the arthroplasty implant of FIG. 2.

FIG. 7 illustrates additional features of the shape memory material connecting member 64. The shape memory material connecting member 64 may include an elongated body 86 having a first threaded portion 88, a second threaded portion 90, and a shaft 92 extending between the first threaded portion 88 and the second threaded portion 90. In an embodiment, the first threaded portion 88 and the second threaded portion 90 include a second diameter D2 that is larger than a first diameter D1 of the shaft 92. The first threaded portion 88 may engage the threaded opening 76 of the proximal interlocking fixation body 60, and the second threaded portion 90 may engage the first threaded opening 80 of the distal interlocking fixation body 62 to connect the shape memory material connecting member 64 to each of the proximal and distal interlocking fixation bodies 60, 62 (see FIG. 4). The shaft 92 may be disposed within the third cannulation 70 of the stem 40.

Figure 8:
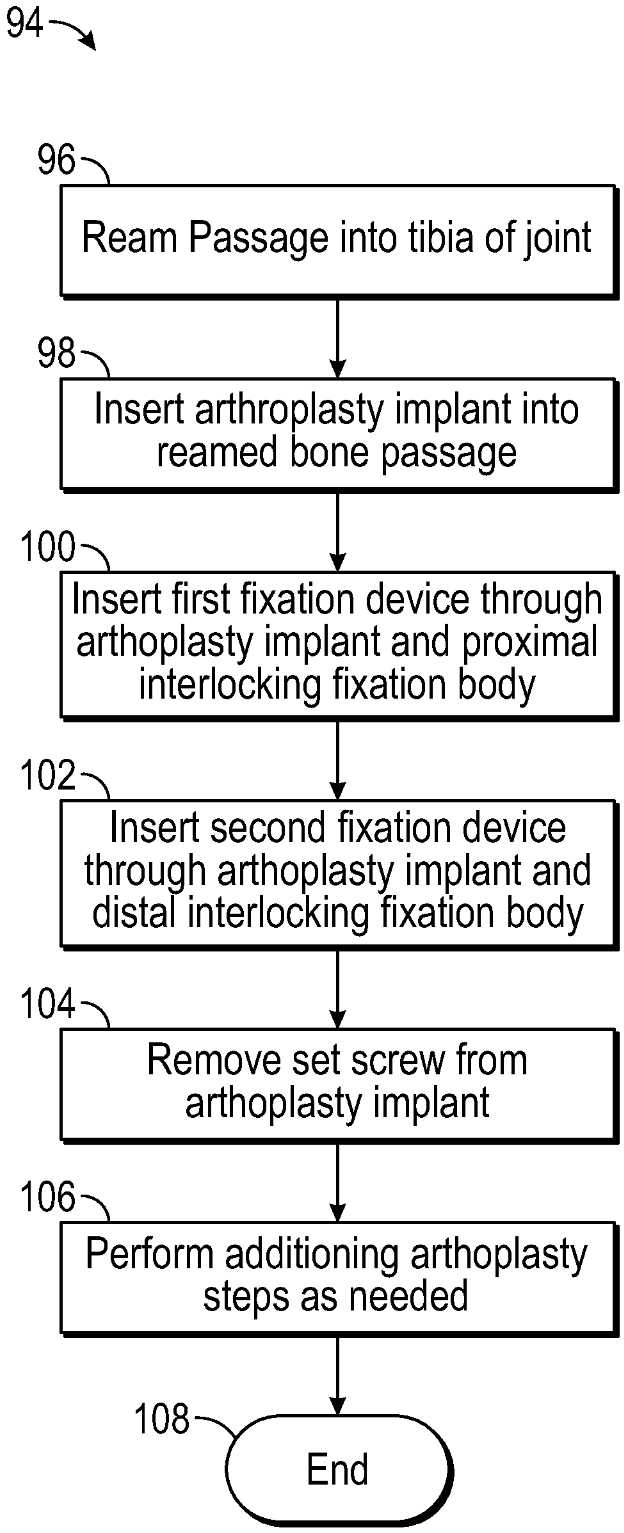
FIG. 8 schematically illustrates an exemplary method for performing an arthroplasty procedure.

FIG. 8, with continued reference to FIGS. 1-7, schematically illustrates a method 94 for performing an arthroplasty procedure. The method 94 may include using the arthroplasty implant 36 to repair or replace diseased portions of the joint 10 of FIG. 1. However, other joints could be repaired or replaced using a similar procedure to the one described below. It should be appreciated that features of the arthroplasty implant 36 may be configured in a specific manner for practicing the method 94 described herein. It should further be understood that the method 94 could include a greater or fewer number of steps and that the steps could be performed in a different order within the scope of this disclosure.

The method 94 may begin at block 96 by reaming a passage into the tibia 18 of the joint 10 for accommodating the arthroplasty implant 36. Any suitable reaming device and reaming technique may be utilized to form the bone passage. Although not specifically described herein, various bone cuts may be made and various bone passages may be formed in order to prepare the joint 10 for receiving the arthroplasty implant 36 and any other implant of the arthroplasty implant system 12.

The arthroplasty implant 36 is inserted into the reamed bone passage at block 98. Placement of the arthroplasty implant 36 may be guided by a targeting device (not shown). Insertion of the arthroplasty implant 36 may require light tapping to insert the arthroplasty implant 36 at the proper distance within the tibia 18. In an embodiment, the shape memory material connecting member 64 is pre-stretched to the stretched position and then held in the stretched position by the holding device 72 prior to inserting the arthroplasty implant 36 into the reamed passage of the tibia 18.

The first fixation device 48 may be inserted through the first opening 46 of the stem 40 and through the non-threaded opening 78 of the proximal interlocking fixation body 60 at block 100. Insertion of the first fixation device 48 in this manner fixates the arthroplasty implant 36 relative to the tibia 18 and substantially locks the proximal interlocking fixation body 60 from further movement relative to the stem 40.

Next, at block 102, the second fixation device 52 may be inserted through the second opening 50 of the stem 40 and through the non-threaded opening 84 of the distal interlocking fixation body 62. Insertion of the second fixation device 52 in this manner further fixates the arthroplasty implant 36 relative to the tibia 18.

The holding device 72 may be backed out and removed from the arthroplasty implant 36 at block 104. In an embodiment, the holding device 72 is unscrewed from the distal interlocking fixation body 62. Removing the holding device 72 from the distal interlocking fixation body 62 allows the shape memory material connecting member 64 to superelastically shorten from the stretched position toward an unstretched position. As the shape memory material connecting member 64 superelastically shortens, the distal interlocking fixation body 62 may move (e.g., slide) within the second opening 50 of the stem 40. The distal interlocking fixation body 62 may therefore operate as a slider inside the stem 40. In an embodiment, the second fixation device 52, which was previously inserted through the distal interlocking fixation body 62, moves toward a proximal end of the second opening 50 (i.e., in a direction toward the proximal interlocking fixation body 60) as the distal interlocking fixation body 62 slides. Since the second fixation device 52 is secured within the tibia 18, the foreshortening of the shape memory material connecting member 64 generates a compressive load that forces the arthroplasty implant 36 and the tibia 18 into further engagement with one another (e.g., the bone is moved against the arthroplasty implant 36 or vice versa). This compressive force is maintained during healing of the joint 10.

Next, at block 106, the surgeon may optionally perform any additional arthroplasty steps needed to complete the arthroplasty repair. The method 94 may end at block 108.

Figure 9:
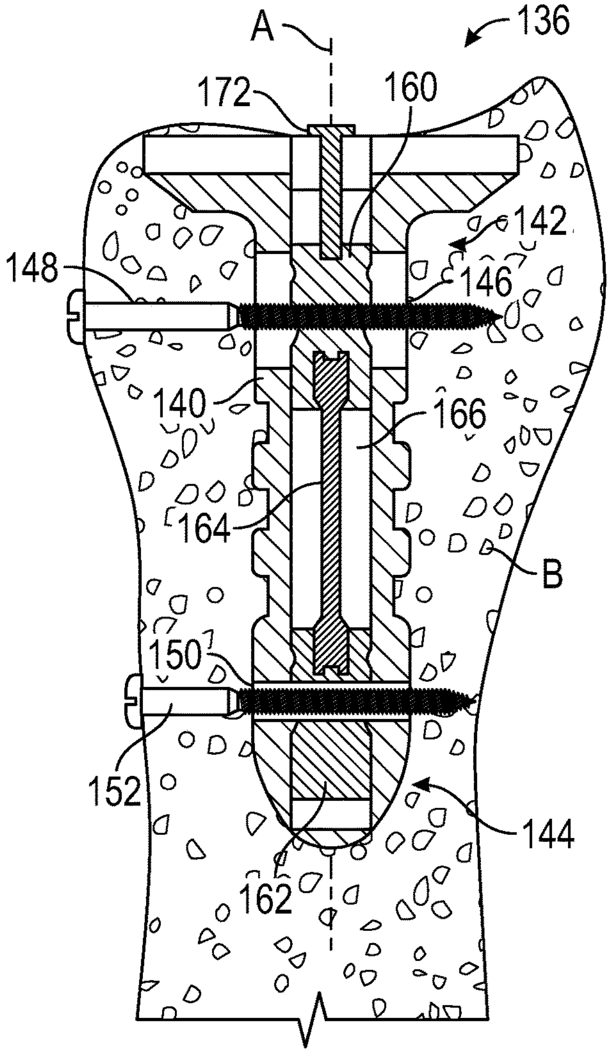
FIG. 9 illustrates another exemplary arthroplasty implant.

FIG. 9 illustrates another exemplary arthroplasty implant 136. The arthroplasty implant 136 may include a stem 140 extending along a longitudinal axis A between a proximal portion 142 and a distal portion 144. The proximal portion 142 of the stem 140 may include a first opening 146 that is configured to receive a first fixation device 148 (e.g., a first screw) for fixating the arthroplasty implant 136 to a long bone B. In an embodiment, the first opening 146 is an elongated slot that extends completely through the stem 140 at a perpendicular angle relative to the longitudinal axis A.

The distal portion 144 of the stem 140 may include a second opening 150 that is configured to receive a second fixation device 152 (i.e., a second screw) for fixating the arthroplasty implant 136 to the long bone B. In an embodiment, the second opening 150 is a round opening that extends completely through the stem 140 at a perpendicular angle relative to the longitudinal axis A. The second opening 150 may extend in parallel with the first opening 146.

The stem 140 of the arthroplasty implant 136 may house a proximal interlocking fixation body 160, a distal interlocking fixation body 162, and a shape memory material connecting member 164. The proximal interlocking fixation body 160, the distal interlocking fixation body 162, and the shape memory material connecting member 164 may be received within one or more cannulations 166 formed inside of the stem 140. The shape memory material connecting member 164 may be connected (e.g., threadably engaged) to both the proximal interlocking fixation body 160 and the distal interlocking fixation body 162.

The arthroplasty implant 136 may additionally include a holding device 172, such as a set screw, which may be used for enacting the superelastic qualities of the shape memory material connecting member 164. In this embodiment, the holding device 172 is removably attached to the proximal interlocking fixation body 160.

The shape memory material connecting member 164 may be pre-stretched to stretched position and then held in the stretched position by the holding device 172. After implantation of the arthroplasty implant 136 within a tunnel of the long bone B, the holding device 172 may be unscrewed or otherwise released from the proximal interlocking fixation body 160. Releasing the holding device 172 allows the proximal interlocking fixation body 160 to slide within the stem 140, thereby allowing the shape memory material connecting member 164 to superelastically shorten toward an unstretched position. Accordingly, in this embodiment, the proximal interlocking fixation body 160 acts a slider rather than the distal interlocking fixation body 162. Releasing the holding device 172 therefore causes the shape memory material connecting member 164 to want to return toward an unstretched position. The arthroplasty implant 136 is therefore equipped applying a constant dynamic compression force between the arthroplasty implant 136 and the long bone B.

Figure 10:
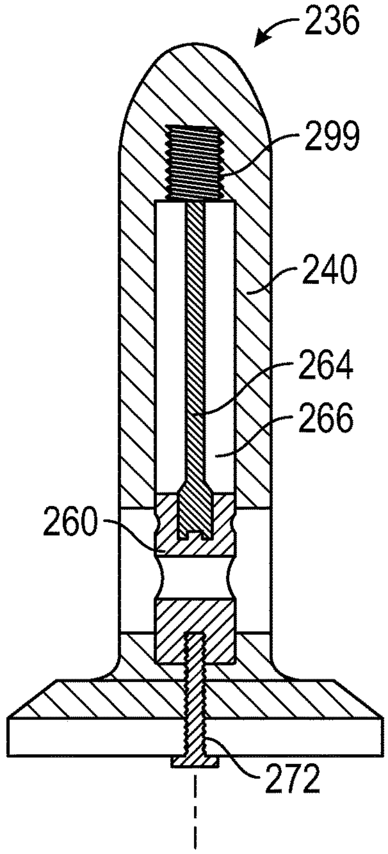
FIG. 10 illustrates yet another exemplary arthroplasty implant.

In yet another embodiment, shown in FIG. 10, an arthroplasty implant 236 may include a single interlocking fixation body 260 that is capable of moving inside a stem 240 of the arthroplasty implant 236. The interlocking fixation body 260 may be housed either proximally or distally inside a cannulation 266 of the stem 240 depending on what joint the arthroplasty implant 236 is applied to. The stem 240 may additionally house a shape memory material connecting member 264. The shape memory material connecting member 264 may be connected (e.g., threadably engaged) at a first end to the interlocking fixation body 260 and at a second end to a threaded passage 299 formed inside the stem 240.

The arthroplasty implant 236 may additionally include a holding device 272, such as a set screw, which may be used for enacting the superelastic qualities of the shape memory material connecting member 264. In an embodiment, the holding device 272 is removably attached to the interlocking fixation body 260. The shape memory material connecting member 264 may be pre-stretched to stretched position and then held in the stretched position by the holding device 272. After implantation of the arthroplasty implant 236 within a bone tunnel, the holding device 272 may be unscrewed or otherwise released from the interlocking fixation body 260, thereby allowing the interlocking fixation body 260 to move within the stem 240 and the shape memory material connecting member 264 to superelastically shorten toward an unstretched position.

This disclosure details novel arthroplasty implants capable of generating and maintaining compressive loads for a prolonged period of time while healing occurs. The compressive loads may be created using shape memory material components that are capable of applying a constant compressive loads between the arthroplasty implants and their surrounding bones. The arthroplasty implants are therefore less prone to migration as compared to known arthroplasty implants.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The term "slider" as used herein refers to a device capable of moving inside an implant. Exemplary sliders include but are not limited to metallic or plastic housings, cages, fasteners, cylinders, plungers, etc.

The term "holding device" as used herein refers to a device that is capable of releasably securing a first device from movement relative to a second device. Exemplary holding devices include but are not limited to set screws, fasteners, retainers, clinches, hooks, pins, pullbacks, spikes, etc.

The implants described herein have referenced surgery in humans. However, the implants of this disclosure can also be used in arthroplasty surgery in other animals, including but not limited to, dogs, horses, cats, cattle, etc.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. An implant system, comprising:

a stem;

an interlocking fixation body translatable within a cannulation of the stem;

a shape memory material connecting member connected to the stem and received within a first threaded opening of the interlocking fixation body; and a holding device removably received within a second threaded opening of the interlocking fixation body and oriented to directly engage the interlocking fixation body to selectively prevent translation of the interlocking fixation body within the cannulation, wherein removal of the holding device permits the shape memory material connecting member to superelastically shorten from a stretched position toward an unstretched position.

2. The implant system as recited in claim 1, wherein the stem extends along a longitudinal axis between a proximal portion and a distal portion, and further wherein the interlocking fixation body is housed within the proximal portion or the distal portion of the stem.

3. The implant system as recited in claim 2, wherein the proximal portion of the stem includes a first stem opening, and the distal portion of the stem includes a second stem opening, and further wherein one of the first stem opening or the second stem opening is an elongated slot and the other of the first stem opening or the second stem opening is a round opening.

4. The implant system as recited in claim 1, wherein the stem includes at least one stem opening configured to receive a fixation device.

5. The implant system as recited in claim 1, wherein the stem is coated with a porous material.

6. The implant system as recited in claim 1, wherein the shape memory material connecting member is a Nitinol (NiTi) rod, wherein the shape memory material connecting member includes an elongated shaft extending between a first threaded portion and a second threaded portion, and further wherein the first threaded portion engages the first threaded opening of the interlocking fixation body and the second threaded portion engages a threaded passage of the stem.

7. The implant system as recited in claim 1, wherein the holding device is a set screw that is removable from the second threaded opening of the interlocking fixation body to allow the shape memory material connecting member to superelastically shorten from the stretched position toward the unstretched position.

8. The implant system as recited in claim 1, wherein a first articulating surface of the implant system is established by a dome of a talar component, and a second articulating surface of the implant system is established by a tray of a tibial component.

9. The implant system as recited in claim 8, wherein the first articulating surface and the second articulating surface are sized and shaped to articulate relative to one another, and further wherein the stem protrudes from a base and is part of the tibial component, and further wherein the base is connected to the tray of the tibial component.

10. The implant system as recited in claim 1, comprising a fixation device received within a non-threaded opening of the interlocking fixation body.

11. The implant system as recited in claim 10, wherein the holding device and the fixation device extend in transverse directions relative to one another.

12. The implant system as recited in claim 1, wherein the holding device is a set screw that engages the second threaded opening of the interlocking fixation body and extends in a direction toward a domed tip of the stem.

13. The implant system as recited in claim 1, wherein the first threaded opening and the second threaded opening are disposed at opposite longitudinal ends of the interlocking fixation body.

14. An implant system, comprising:

a stemmed implant including a base and a stem that protrudes outwardly from the base along a longitudinal axis between a proximal portion and a distal portion;

an interlocking fixation body movably disposed within the stem;

a shape memory material rod connected at one end to the interlocking fixation body and at another end to the stem; and a set screw removably connected to a threaded opening of the interlocking fixation body, wherein the set screw directly contacts a complementary surface of the interlocking fixation body to mechanically lock the interlocking fixation body against translation relative to the stem until the set screw is removed from the threaded opening, wherein the set screw extends along the longitudinal axis in a direction toward a domed tip located at the proximal portion of the stem.

15. The implant system as recited in claim 14, wherein the set screw is received through a bottom surface of the base.

16. The implant system as recited in claim 14, wherein a first articulating surface of the implant system is established by a dome of a first component of the implant system, and a second articulating surface is established by a tray of a second component of the implant system, and further wherein the first articulating surface and the second articulating surface are sized and shaped to articulate relative to one another, and further wherein the tray of the second component is connected to the base of the stemmed implant.

17. The implant system as recited in claim 14, wherein the implant system is a total ankle arthroplasty implant system.

18. The implant system as recited in claim 14, comprising a fixation device received through a non-threaded opening of the interlocking fixation body.

19. The implant system as recited in claim 14, wherein the base is enlarged relative to the stem.

20. The implant system as recited in claim 18, wherein the set screw and the fixation device extend along orthogonal paths.

* * * * *